(12) United States Patent
Dhaniyala et al.

(10) Patent No.: US 9,752,973 B2
(45) Date of Patent: Sep. 5, 2017

(54) METHODS AND SYSTEMS FOR MULTIPLE CHARGE CORRECTION OF ELECTRICAL MOBILITY SPECTROMETER DATA

(71) Applicants: Suresh Dhaniyala, Potsdam, NY (US); Meilu He, Potsdam, NY (US)

(72) Inventors: Suresh Dhaniyala, Potsdam, NY (US); Meilu He, Potsdam, NY (US)

(73) Assignee: CLARKSON UNIVERSITY, Potsdam, NY (US)

( * ) Notice: Subject to any disclaimer, the term of this patent is extended or adjusted under 35 U.S.C. 154(b) by 745 days.

(21) Appl. No.: 14/169,697

(22) Filed: Jan. 31, 2014

(65) Prior Publication Data

US 2014/0214337 A1 Jul. 31, 2014

Related U.S. Application Data

(60) Provisional application No. 61/759,021, filed on Jan. 31, 2013.

(51) Int. Cl.
*G01N 31/00* (2006.01)
*G01N 15/02* (2006.01)
*G01N 15/00* (2006.01)

(52) U.S. Cl.
CPC . *G01N 15/0266* (2013.01); *G01N 2015/0003* (2013.01)

(58) Field of Classification Search
CPC .................... G01N 2001/2223; G11C 13/04
See application file for complete search history.

(56) References Cited

U.S. PATENT DOCUMENTS 6,803,763 B2 * 10/2004 Peters .............. G01R 33/56554
324/318

OTHER PUBLICATIONS

Sun et al., "Grain-size Distribution Funciton of Poly-modal Sediments in Hyraulic and Aeolian Environments , and Numerical Partioning of the Sedimentary Components," 2002, Sedimentary Geology Publication, vol. 152, pp. 263-277.*

* cited by examiner

*Primary Examiner* — Elias Desta
(74) *Attorney, Agent, or Firm* — Bond Schoeneck & King, PLLC; George McGuire; Blaine Bettinger (57) ABSTRACT

Systems and methods for determining particle size distribution from electrical mobility spectrometry (EMS) measurements in the presence of multiply charged particles. EMS data comprising zeroth order singly-charged particle size distribution information for one or more EMS channels is obtained and fitted using a Gumbel distribution function to obtain a fit function value. The obtained fit function value is used to correct for multiply-charged particle contribution to the received EMS data.

20 Claims, 10 Drawing Sheets

METHODS AND SYSTEMS FOR MULTIPLE CHARGE CORRECTION OF ELECTRICAL MOBILITY SPECTROMETER DATA

CROSS-REFERENCE TO RELATED APPLICATIONS

This application claims priority to U.S. Provisional Patent Application Ser. No. 61/759,021, filed on Jan. 31, 2013 and entitled "Multiple Charging Correction Algorithm for Scanning Electrical Mobility Spectrometer Data," the entire disclosure of which is incorporated herein by reference.

STATEMENT REGARDING FEDERALLY SPONSORED RESEARCH

This invention was made with government support under grant number AGS1126361 awarded by the National Science Foundation (NSF). The government has certain rights in the invention.

BACKGROUND

The present invention relates to methods for electrical mobility spectrometry and, more particularly, to methods for multiple-charge correction of SEMS data.

Electrical mobility spectrometers and scanning electrical mobility spectrometers ("SEMS") are commonly used for size distribution measurements of sub-micron particles. SEMS measurements require particles to be charged and this is often achieved by passing them through a bipolar diffusion charger, where the particles acquire an equilibrium charge distribution. The charged particles are then classified according to their electrical mobilities in a differential mobility analyzer ("DMA") or any other mobility classifier. The number concentrations of the classified particles can be obtained using a particle detector, such as a condensation particle counter ("CPC") or an electrometer.

To determine the size distribution of the sampled particles, the number concentration data of the mobility-classified particles must be inverted considering the instrument characteristics. If the DMA is operated under high resolution and the presence of multiply-charged particles can be ignored, the particle size distributions can be determined straightforwardly from the measured signal using a singly-charged, zeroth order inversion approach.

To account for the contribution of multiply-charged particles to the measured signal, a correction to the singly charged size distribution is required. This correction typically requires accurate knowledge of the largest particles sampled into the DMA, and a practical implementation of this requirement is achieved using an inertial impactor upstream of the aerosol sample flow that eliminates all particles beyond a critical size. Under ideal DMA and impactor operation, this approach will result in accurate size distribution measurements.

SEMS measurements are sometimes made under a range of non-ideal conditions, including: absence of an upstream impactor, non-ideal operation of the impactor, and/or operation under a partial voltage scan range. Under high-flow or low-pressure operation of a DMA, the pressure drop across the impactor may be problematic and under such conditions, the DMA may be operated without an impactor.

Even if an impactor is used upstream of the DMA, the discrepancy between the particle aerodynamic size that determines the impactor efficiency and the mobility size relevant to DMA measurements could complicate size distribution calculation from SEMS measurements. For example, SEMS measurements of size distributions of soot agglomerate or carbon nanotube particles were found to be affected by the difficulty of impacting out particles larger than the impactor cut-size. Even when the mobility and aerodynamic sizes are matched, the impactor is only effective if its cut-size matches the largest singly-charged particle size that can be classified by the DMA. When the DMA operating conditions may not permit scanning to the highest design voltage, such as when the DMA is operated on an aircraft where the upper limit of the voltage operation is pressure-dependent, the impactor cut-size may not match upper size limit of the DMA.

Accordingly, there is a continued need for multiple-charge correction of SEMS data.

BRIEF SUMMARY

Disclosed herein are systems and methods for determining particle size distribution from electrical mobility spectrometry and scanning electrical mobility spectrometry measurements in the presence of multiply charged particles. SEMS data comprising zeroth order singly-charged particle size distribution information for one or more SEMS channels is obtained and fitted using a Gumbel distribution function to obtain a fit function value. The obtained fit function value is used to correct for multiply-charged particle contribution to the received SEMS data.

According to a first aspect is a method for determining particle size distribution from electrical mobility spectrometry (EMS) measurements in the presence of multiply charged particles, the method comprising the steps of: (i) receiving EMS data, wherein the received EMS data comprises a particle signal for one or more EMS channels; (ii) calculating a zeroth order singly-charged particle size distribution from the particle signals in the one or more EMS channels; (iii) fitting, using a distribution function, the received zeroth order singly-charged particle size distribution to obtain a fit function value; and (iv) correcting, using the obtained fit function value, for multiply-charged particle contribution to the received EMS data.

According to an embodiment, the EMS is a scanning electrical mobility spectrometer.

According to an embodiment, the EMS data is obtained without the use of an inertial impactor.

According to an embodiment, the distribution function is a Gumbel distribution function, a lognormal distribution function, or a bi-lognormal distribution function.

According to an embodiment, the method further comprises the step of interpolating the obtained zeroth order singly-charged particle size distribution into one or more finer channels to determine an appropriate number of fit points for said fitting step.

According to an embodiment, wherein if said interpolation determines that there is no detected mode size, or if said interpolation determines that a separate mode is beginning near the end of the obtained EMS data, then approximately the last 5 data points are used for said fitting step.

According to an embodiment, the distribution function is a Gumbel distribution function, and the method further comprises the step of determining an initial value for $D_{pg}$, $\sigma_g$, and $N_t$ for the Gumbel distribution function.

According to an embodiment, the initial value for $D_{pg}$ is equal to a particle size with the maximum concentration value.

According to an embodiment, the initial value for $N_t$ is a number concentration obtained from an integral of the singly-charged distribution $dN/d \log D_{p,i}$.

According to an embodiment, the correcting step is performed using multiple-charge correction.

According to an embodiment, the method further comprises the step of obtaining said EMS data using an EMS.

In another aspect is a non-transitory machine readable storage medium having stored thereon a computer program for determining particle size distribution from electrical mobility spectrometry (EMS) measurements in the presence of multiply charged particles, the computer program comprising instructions for causing the machine to perform the steps of: (i) receiving EMS data, wherein the received EMS data comprises a particle signal for one or more EMS channels; (ii) calculating a zeroth order singly-charged particle size distribution from the particle signals in the one or more EMS channels; (iii) fitting, using a distribution function, the received zeroth order singly-charged particle size distribution information to obtain a fit function value; and (iv) correcting, using the obtained fit function value, for multiply-charged particle contribution to the received EMS data.

According to an embodiment, the distribution function is a Gumbel distribution function.

According to an embodiment, the computer program further comprises instructions for causing the machine to interpolate the obtained zeroth order singly-charged particle size distribution information into one or more finer channels to determine an appropriate number of fit points for said fitting step.

In another aspect is a system configured to determine particle size distribution from electrical mobility spectrometry (EMS) measurements in the presence of multiply charged particles, the system comprising: (i) a scanning electrical mobility spectrometry configured to obtain data, wherein the received EMS data comprises a particle signal for one or more EMS channels; and (ii) a processor configured to: (a) calculate a zeroth order singly-charged particle size distribution from the particle signals in the one or more EMS channels; (b) fit, using a distribution function, the received zeroth order singly-charged particle size distribution to obtain a fit function value; and (c) correct, using the obtained fit function value, for multiply-charged particle contribution to the received EMS data.

According to an embodiment, the EMS data is obtained using a scanning electrical mobility spectrometer.

According to an embodiment, the EMS data is obtained without the use of an inertial impactor.

According to an embodiment, the distribution function is a Gumbel distribution function.

According to an embodiment, the processor is further configured to interpolate the obtained zeroth order singly-charged particle size distribution information into one or more finer channels to determine an appropriate number of fit points for said fitting step.

According to an embodiment, the distribution function is a Gumbel distribution function, and wherein said processor is further configured to determine an initial value for $D_{pg}$, $\sigma_g$, and $N_t$ for the Gumbel distribution function.

BRIEF DESCRIPTION OF THE SEVERAL VIEWS OF THE DRAWING(S)

The present invention will be more fully understood and appreciated by reading the following Detailed Description in conjunction with the accompanying drawings, in which.

DETAILED DESCRIPTION

According to an embodiment provided are methods for retrieving accurate particle size distribution from SEMS measurements in the presence of multiply charged particles, thereby providing multiple-charge correction of SEMS data. According to an embodiment, the zeroth order singly charged particle size distribution is fit using a Gumbel distribution function, and the resultant fit is used to correct for the multiply-charged contribution to the SEMS data.

According to one aspect is a method for multiple charge correction of SEMS data, where the SEMS data can be obtained without an inertial impactor upstream of the differential mobility analyzer. The singly-charged distribution obtained from the SEMS data is fit with an appropriate fit function, including but not limited to the Gumbel distribution, and the fit function values are used to estimate the contribution of multiply-charged particles beyond the DMA scan range to the last few channels of the SEMS data.

Particle Size Distribution Retrieval

For charged particles entering a cylindrical DMA, the centroid mobility, $Z^*_p$, of the classified particles extracted out of the DMA can be expressed as:

$$Z^*_p = \frac{Q_{sh} + Q_{ex}}{4\pi LV} \ln\left(\frac{R_2}{R_1}\right) \quad \text{(Equation 1)}$$

where $Q_{sh}$ is the DMA sheath flow rate, $Q_{ex}$ is the DMA excess flow rate, $R_1$ and $R_2$ are the inner and outer radii of the classification section, respectively, V is the voltage applied to the inner cylinder, and L is the length of the classifier section. For size distribution measurements, the particle electrical mobility must be related to their mobility-equivalent diameter. For a spherical particle of diameter $D_p$, or a non-spherical particle with a volume-equivalent diameter $D_{ve}$, the mobility-diameter relation is:

$$Z_p = \frac{neC_c(D_p)}{3\pi\mu D_p} \quad \text{(Equation 2)}$$
$$= \frac{neC_c(D_{ve})}{3\pi\mu\chi D_{ve}}$$

where n is the number of elementary charges on the particle, e is the elementary charge, $C_c$ is the Cunningham slip correction, $\mu$ is the gas viscosity, and X is the dynamic shape factor. For a distribution of charges, the mobility-classified particles from a DMA will, thus, consist of particles different sizes.

In a SEMS measurement system, particles of an unknown size distribution, $dN/d\log D_p$, are passed through a bipolar charger, where a fraction of particles, $f_c$, of diameter $D_p$ acquire n charges and the charged particles are then mobility-classified in a DMA, and the classified particles are finally detected by a CPC. The CPC signal [concentration; S(V)] associated with the DMA classification voltage V, can be related to the DMA operating conditions as:

$$S(V) = \sum_{n=1}^{\infty} \frac{Q_a}{Q_s} \int_0^{\infty} \eta_{DMA}(D_p)\eta_{CPC}(D_p) \quad \text{(Equation 3)}$$
$$\Omega(V, n, D_p)f_c(D_p, n)\frac{dN}{d\log D_p}d\log D_p$$

where $\Omega(V, D_p, n)$ is the DMA transfer function, representing the probability of extracting particles of diameter $D_p$ with n charges, at a DMA classification voltage, $V_{nDMA}$ is the size-dependent DMA penetration efficiency, $\eta_{CPC}$ is the size-dependent CPC detection efficiency, and $Q_a$ and $Q_s$ are the incoming aerosol and outgoing sample flow rates of the DMA, respectively. The SEMS equation has the form of the Fredholm integral equation of the first kind, with the additional complication of the summation term associated with the multiple charge contribution. Different solution approaches to determine particle size distributions from the signal equation are described below.

Zeroth Order, Singly-Charged Inversion

Assuming only the presence of singly charged particles and considering a DMA operating at high resolution such that only particles of a narrow diameter range are classified out, the SEMS signal equation can be rewritten as:

$$S(V) = \frac{Q_a}{Q_s}\eta_{DMA}(D^*_{p,1})\eta_{CPC}(D^*_{p,1})f_c(D^*_{p,1}, 1)\frac{dN}{d\log D_p}\bigg|_{D^*_{p,1}} \quad \text{(Equation 4)}$$

$$\int_0^{\infty} \Omega(V, Z_p)\frac{d\log D_p}{dZ_p}dZ_p$$

where $D^*_{p,1}$ is the diameter of singly-charged particles corresponding to the centroid mobility of the transfer function, $Z^*_p$ calculated using Equation 2, above. Considering the mobility-diameter relationship, the SEMS equation reduces to:

$$S(V) = \quad \text{(Equation 5)}$$
$$\frac{Q_a}{Q_s}\eta_{DMA}(D^*_{p,1})\eta_{CPC}(D^*_{p,1})f_c(D^*_{p,1}, 1)\frac{1}{2.303a^*_1}\frac{dN}{d\log D_p}\bigg|_{D^*_{p,1}}$$

$$\int_0^{\infty} \Omega(V, \tilde{Z}_p)d\tilde{Z}_p$$

where, $\tilde{Z}_p$ is the non-dimensional mobility, defined as $Z_p/Z^*_p$ and the mobilities $Z^*_p$ and $Z_p$ are expressed in Equations (1) and (2), respectively.

For an ideal transfer function, the area of the transfer function, i.e., $$\int_0^{\infty} \Omega(V, \tilde{Z}_p)d\tilde{Z}_p, \quad \text{(Equation 5.1)}$$

is $\beta(1 + \delta)$ where $\beta$ and $\delta$ are non-dimensional flow parameters:

$$\beta = \frac{Q_s + Q_a}{Q_{sh} + Q_{ex}} \quad \text{(Equation 6)}$$

$$\delta = \frac{Q_s - Q_a}{Q_s + Q_a} \quad \text{(Equation 7)}$$

Therefore, the size distribution can be determined from the zeroth-order inversion of the SEMS signal as:

$$\frac{dN}{d\log D_p}\bigg|_{D_{p,1}^*} = \frac{S(V)}{\frac{Q_a}{Q_s}\eta_{DMA}(D_{p,1}^*)\eta_{CPC}(D_{p,1}^*)} \quad \text{(Equation 8)}$$

$$f_c(D_{p,1}^*,1)\frac{1}{2.303a_1^*}\beta(1+\delta)$$

where:

$$a_1^* = -\frac{d\ln Z_p}{d\ln D_p}\bigg|_{D_{p,1}^*} \quad \text{(Equation 9)}$$

$$= \frac{1+2\alpha_1 Kn + \alpha_2 e^{\alpha_3/Kn}(2Kn+\alpha_3)}{1+Kn(\alpha_1+\alpha_2 e^{\alpha_3/Kn})}$$

where $\alpha_1=1.209$, $\alpha_2=0.406$, and $\alpha_3=0.893$ are coefficients of slip correction factor, $C_c$ and Kn is the particle Knudsen number:

$$Kn = \frac{2\lambda}{D_{p,1}^*} \quad \text{(Equation 10)}$$

where $\lambda$ is the air mean free path.

The accuracy of the zeroth order singly-charged size distribution calculation approach (Equation 8) is dependent on the nature of the sampled particle size distribution and this is illustrated by considering two sample size distribution scenarios. The SEMS operating conditions and the particle size distributions considered in the test scenarios are listed in Table 1.

TABLE 1

SEMS operating conditions and test size distributions sent to the SEMS system

| | SEMS Operating Condition | | | | Particle Size Distribution | | |
|---|---|---|---|---|---|---|---|
| Case No. | $Q_{sh}$ (lpm) | $Q_a$ (lpm) | $V_{min}$ (V) | $V_{max}$ (V) | $\overline{D_{pl}}$ (nm) | $\sigma_1$ | $N_t(\text{cm}^{-3})$ |
| A | 6 | 0.6 | 10 | 10,000 | 50 | 1.6 | 1000 |
| B | 6 | 0.6 | 10 | 10,000 | 250 | 2.0 | 1000 |
| C | 6 | 0.6 | 10 | 2,000 | 50 | 1.6 | 1000 |
| D | 6 | 0.6 | 10 | 2,000 | 250 | 2.0 | 1000 |
| E | 3 | 0.3 | 10 | 10,000 | — | — | — |

Figure 1:
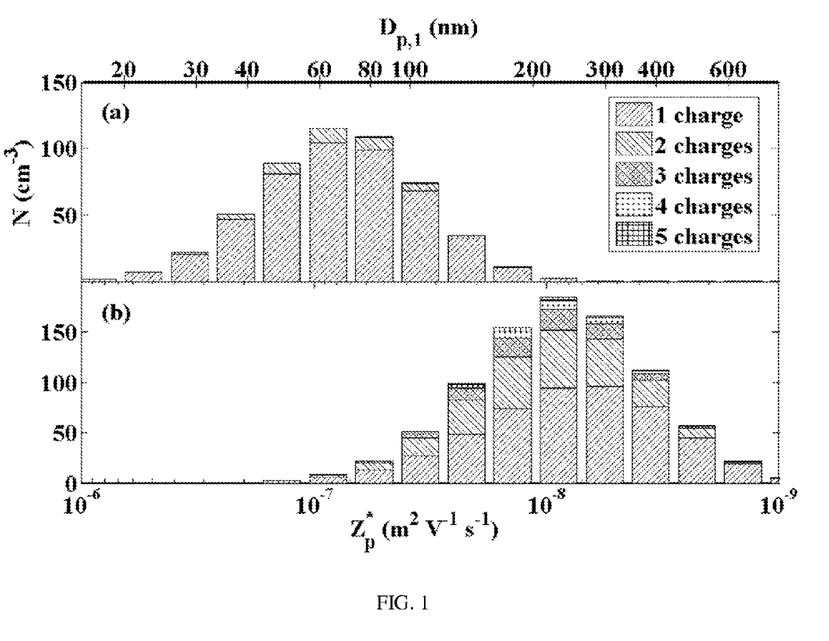
FIG. 1 is a graph representing the contribution of multiply-charged particles to the SEMS signal distribution is shown for two cases listed in TABLE 1 below, where (a) is case A from TABLE 1 and (b) is case B TABLE 1.
Figure 2:
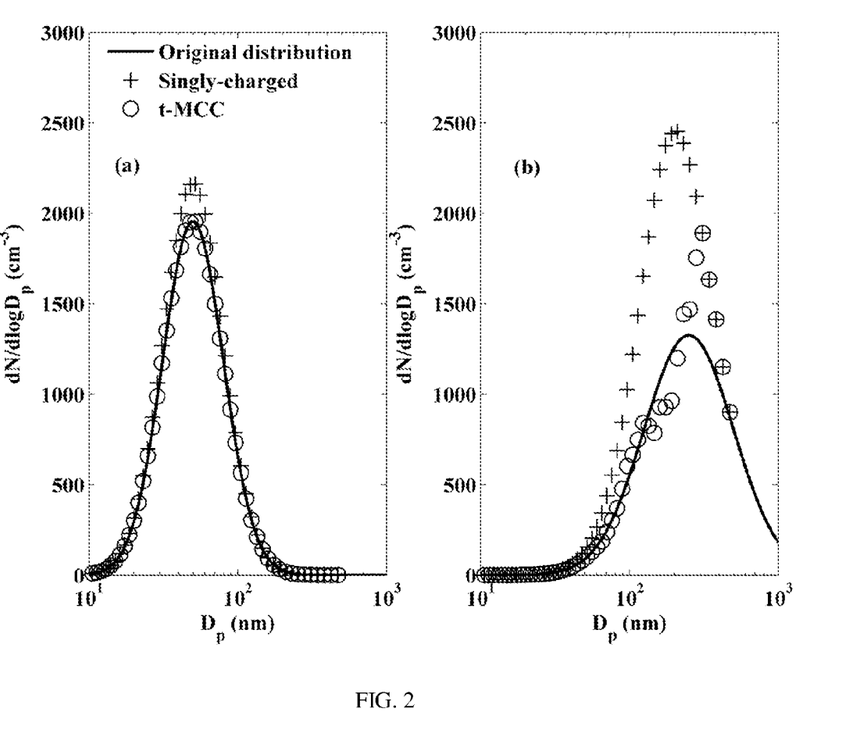
FIG. 2 is a graph representing the particle size distributions determined from SEMS channel data considering only singly-charged particles (Eq. 8) and traditional multiple-charge correction (t-MCC) method, where the calculated size distributions are compared against the original distribution for two cases of SEMS operating conditions and the particle size distributions listed in TABLE 1 below, where (a) is case A from TABLE 1 and (b) is case B TABLE 1.

In the first scenario (case A in Table 1), particles are considered to be largely in the ultrafine size range and their mobility distribution, assuming they are charged by a bipolar diffusion charger, is shown in FIG. 1a. For this scenario, the fraction of multiply charged particles at any selected mobility is seen to be small and, thus, the size distribution calculated considering only the presence of singly-charged particles (Equation 8) largely matches the original size distribution (FIG. 2a). For the second scenario, a particle size distribution with a significant fraction of particles larger than 100 nm is considered (case B in Table 1). In this case, the fraction of multiply charged particles in lower mobility channels is high (FIG. 1b), and correspondingly, there is a significant discrepancy between the size distribution calculated using Equation 8 and the original particle size distributions (FIG. 2b). As SEMS measurements are often made under conditions with significant fraction of particle diameter larger than 100 nm, the contribution of multiply-charged particles must be considered in any size distribution calculation approach.

Traditional Multiple Charging Correction Method

Considering the presence of multiply-charged particles, and assuming that the DMA is operated at a high resolution, then the SEMS signal can be related to the size distribution as:

$$S(V) = \quad \text{(Equation 11)}$$

$$\frac{Q_a}{Q_s}\left\{\begin{array}{l}\left[\eta_{DMA}(D_{p,1}^*)\eta_{CPC}(D_{p,1}^*)f_c(D_{p,1}^*,1)\frac{dN}{d\log D_p}\bigg|_{D_{p,1}^*}\int_0^\infty \Omega(V,1,D_p)d\log D_p\right] \\ + \sum_{n=2}^\infty\left[\eta_{DMA}(D_{p,n}^*)\eta_{CPC}(D_{p,n}^*)f_c(D_{p,n}^*,n)\frac{dN}{d\log D_p}\bigg|_{D_{p,n}^*}\int_0^\infty \Omega(V,n,D_p)d\log D_p\right]\end{array}\right\}$$

where $D^*_{p,n}$ is the particle diameter with n charges corresponding to the mean electrical mobility, $Z^*_p$, classified at voltage V. The SEMS signal can, thus, be considered as a combination of two signals, corresponding to the two terms on the right-hand side of Equation (11), expressed as:

$$S(V)=S_f(V)+S_m(V) \quad \text{(Equation 12)}$$

where $S_f(V)$ is the SMS signal at voltage V, corresponding to singly-charged particles and $S_m(V)$ is the contribution of multiply-charged particles to the SEMS signal. If the multiple-charge contribution to the signal is known, then the size distribution at any SEMS channel, i, can be calculated similar to the zeroth order solution obtained above, as:

$$\frac{dN}{d\log D_p}\bigg|_{D_{p,1}^*} = \frac{S^i(V)-S_m^i(V)}{\frac{Q_a}{Q_s}\eta_{DMA}(D_{p,1}^{*,i})\eta_{CPC}(D_{p,1}^{*,i})} \quad \text{(Equation 13)}$$

$$f_c(D_{p,1}^{*,i},1)\frac{1}{2.303a_1^{*,i}}\beta(1+\delta)$$

where $D_{p,1}^{*,i}$ is the diameter of singly-charged particles corresponding to the mean classified mobility at $i^{th}$ channel.

Using Equation 13, the size distribution can be correctly retrieved for all channels. If the SEMS instrument can be scanned to high enough voltages such that the largest particle sizes present in the aerosol flow can be classified out as singly charged, then the assumption of the singly charged inversion (Equation 8) is accurate for the size distribution value in the last channel (M). If there are no particles in size range beyond the DMA scan voltage, then the multiple charge contribution to the signal at $(M-1)^{th}$ channel can be calculated as:

$$S_m^{M1} = \quad \text{(Equation 14a)}$$

-continued $$\frac{Q_a}{Q_s}\beta(1+\delta)\sum_{n=2}^{\infty}\left[\frac{1}{2.303 a_n^{*,M1}}\eta_{DMA}(D_{p,n}^{*,M1})\eta_{CPC}(D_{p,n}^{*,M1})\right.$$

$$\left. f_c(D_{p,n}^{*,M1},n)\frac{dN}{d\log D_p}\bigg|_{D_{p,n}^{*,M1}}\right]$$

where $D_{p,n}^{*,M-1}$ is the diameter of particles with n charges corresponding to the classification voltage of channel M−1, the coefficient $a_n^{*,M-1}$ is determined using Equation (9) with the Knudsen number calculated based on the particle diameter $D_{p,n}^{*,M-1}$. From Equations (13) and (14a), the multiple-charge corrected size, distribution value for the $(M-1)^{th}$ channel can be determined. Following this procedure, the multiple charge correction can be made to all channels stepping down from the $(M-1)^{th}$ channel to the first channel, with the multiple charge contribution to the signal at the $i^{th}$ channel expressed as:

$$S_m^i = \frac{Q_a}{Q_s}\beta(1+\delta)\sum_{n=2}^{\infty}\left[\frac{1}{2.303 a_n^{*,i}}\eta_{DMA}(D_{p,n}^{*,i})\right. \quad \text{(Equation 14b)}$$

$$\left.\eta_{CPC}(D_{p,n}^{*,i})f_c(D_{p,n}^{*,i},n)\frac{dN}{d\log D_p}\bigg|_{D_{p,n}^{*,i}}\right]$$

Thus, the multiple-charge correction approach described above can be summarized as:

(1). Calculate the size distribution assuming only singly-charged particles using Equation (8).

(2). If there are no particles beyond the DMA size range, for the penultimate channel, M−1, calculate the multiple-charge contribution to the SEMS signal, $S_m^{M-1}$ using Equation (14a) and considering from the size distribution calculated in Step (1).

(3). Update the size distributions with the multiple charge correction following Equation (13)

(4). Repeat above steps for all channels, stepping backwards from the penultimate channel to the first. Note, that to calculate the values of $$\frac{dN}{d\log D_p}\bigg|_{D_{p,n}^{*,i}}$$

for the multiple charge correction (Eq. 14) at channel i, interpolation of the discrete size distribution, $$\frac{dN}{d\log D_p}\bigg|_{D_{p,1}^{*,i}}$$

will be required.

The above approach to account for multiple charge correction (MCC) is referred to herein as the traditional MCC method (labeled in the figures as t-MCC).

The accuracy of the MCC method can be illustrated by revisiting the two scenarios considered for testing the singly-charged inversion calculation approach. For the first case (case A), i.e. particles largely in the ultrafine size range, the DMA voltage scan range can be assumed to cover the entire size distribution and hence the particle concentration in the last channel will be zero. Under this scenario, the size distribution calculated with the traditional MCC method described above is seen to agree very well with the original size distribution (FIG. 2a). For the second case (case B), where the size distribution extends past the DMA scan range, and thus the condition noted in step 2 of the traditional MCC method is violated, the traditional MCC method fails to obtain the correct size distribution (FIG. 2b).

Figure 3:
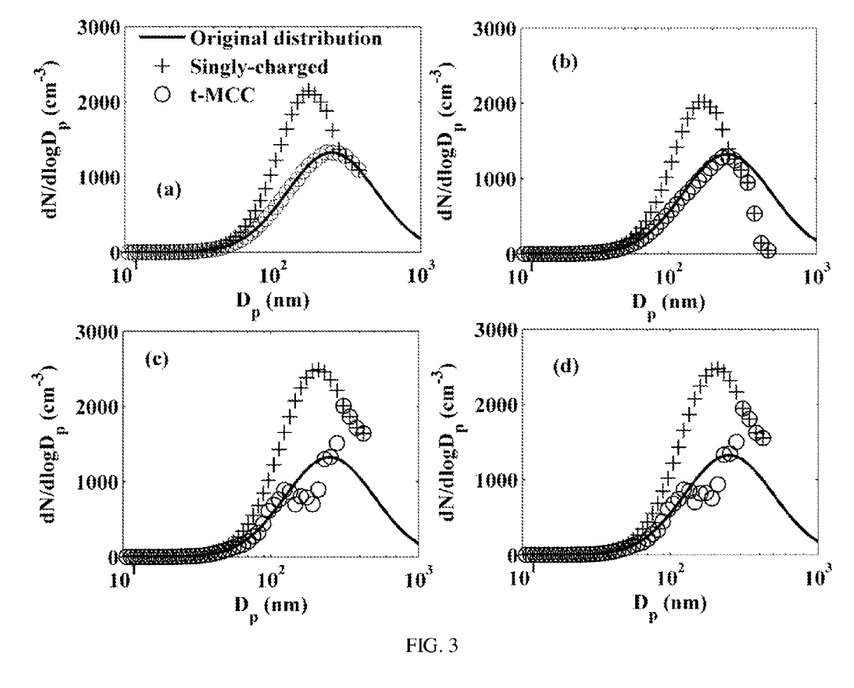
FIG. 3 is a graph representing the comparison of particle size distributions calculated using the singly charged and traditional MCC method when an impactor is present upstream of the SEMS for the following cases: (a) matched aerodynamic and mobility sizes; (b) aerodynamic size smaller than mobility size; spherical particles; density>1.0 g cm-3; (c) aerodynamic size larger than mobility size; spherical particles with density of 0.2 gcm-3; and (d) aerodynamic size larger than mobility size; particle shape factor of 1.5; density of 1.0 g cm-3.

If an ideal, sharp cut-size inertial impactor is placed upstream of the DMA, and the impactor cutoff size is selected to match the singly-charged particle size in the last SEMS channel, then the size distribution calculated using the traditional MCC approach is seen to result in accurate size distribution calculation for the second scenario (FIG. 3a). Note that, if the impactor has a size-dependent collection efficiency curve, $\eta_{impactor}(D_p)$, then the size distribution $$\frac{dN}{d\log D_p}\bigg|_{MCC}^{impactor}$$

obtained from the traditional MCC approach must be corrected considering the impactor collection curve as:

$$\frac{dN}{d\log D_p}\bigg|_{MCC} = \quad \text{(Equation 15)}$$

$$\frac{dN}{d\log D_p}\bigg|_{MCC}^{impactor} / [1-\eta_{impactor}(D_p)] \text{ for } \eta_{impactor}(D_p) \geq 0$$

These tests suggest that accurate size distribution calculation with the traditional MCC method is only possible if all particle sizes entering the DMA can be extracted out as singly charged and this requires the incoming particles to be entirely scanned by the DMA or an impactor located upstream of the DMA, with its cut-size designed to match the largest singly-charged particle diameter extracted from the DMA.

Relationship Between Aerodynamic Size and Mobility Size

The particle aerodynamic size, relevant for inertial impaction, and its mobility size, relevant for SEMS measurements, may not always match. The aerodynamic size of a particle can be related to its volume equivalent size, $D_{ve}$ as:

$$D_a = D_{ve}\sqrt{\frac{1}{\chi}\frac{\rho_p}{\rho_0}\frac{C_c(D_{ve})}{C_c(D_a)}} \quad \text{(Equation 16)}$$

where $\rho_p$ is the particle density, $\rho_0$ is the reference density (1.0 g cm-3). Combining Equations (2) and (16), the relationship between mobility size and aerodynamic size can be expressed as:

$$D_p = D_a\sqrt{\chi^3\frac{C_c^2(D_p)C_c(D_a)}{C_c^3(D_{ve})}\frac{\rho_0}{\rho_p}} \quad \text{(Equation 17)}$$

For a typical SEMS operation, the cut-size of the impactor is >~200 nm, and under these conditions, the slip correction factor ratio, $C_c^2(D_p) C_c(D_a)/C_c^3(D_{ve})$ can be reasonably assumed to equal 1. Therefore, the particle density and shape factor are the only two factors that determine the relationship between the aerodynamic and mobility sizes. For a solid spherical particle of unit density (1.0 g cm$^{-3}$), the mobility size and the aerodynamic size are identical. For these particles, the size distribution can be successfully retrieved from SEMS measurement signals using the traditional MCC method if the correction associated with the impactor collection efficiency curve (Equation 15) is considered, as illustrated in FIG. 3a for case B. For solid spherical particles of density larger than 1.0 g cm$^{-3}$, i.e., particle mobility size is smaller than the aerodynamic size, however, the particle size distribution cannot be correctly retrieved because the impactor collection efficiency curve is described by the aerodynamic size. For example, for the size distribution scenario in case B, the mean particle diameter of the last SEMS channel is 473 nm, and if the impactor aerodynamic cut-off diameter is 473 nm corresponding to the equivalent mobility diameter 375 nm, then the size distribution obtained using the traditional MCC method is shown in FIG. 3b, which deviates from the original particle size distribution.

When the particle density, $\rho_p$, is less than 1 g cm$^{-3}$, or when the shape factor is higher than 1, then the mobility sizes are larger than the aerodynamic size and under these conditions, again accurate particle size distributions cannot be obtained with the traditional MCC method. For example, consider the SEMS size distribution measurement of fumed silica particles that have a density of 0.2 g cm$^{-3}$. For this case, the impactor does not eliminate the particles beyond the scan range from the aerosol flow of the DMA and hence the inversion of SEMS data with the traditional MCC does not result in accurate size distribution calculation (FIG. 3c). Similarly, even if the particles have a density of 1.0 g cm$^{-3}$, but are non-spherical with a shape factor of 1.5, the traditional MCC method cannot accurately recover the size distribution from the SEMS data (FIG. 3d).

Partial Scanning of SEMS

Figure 4:
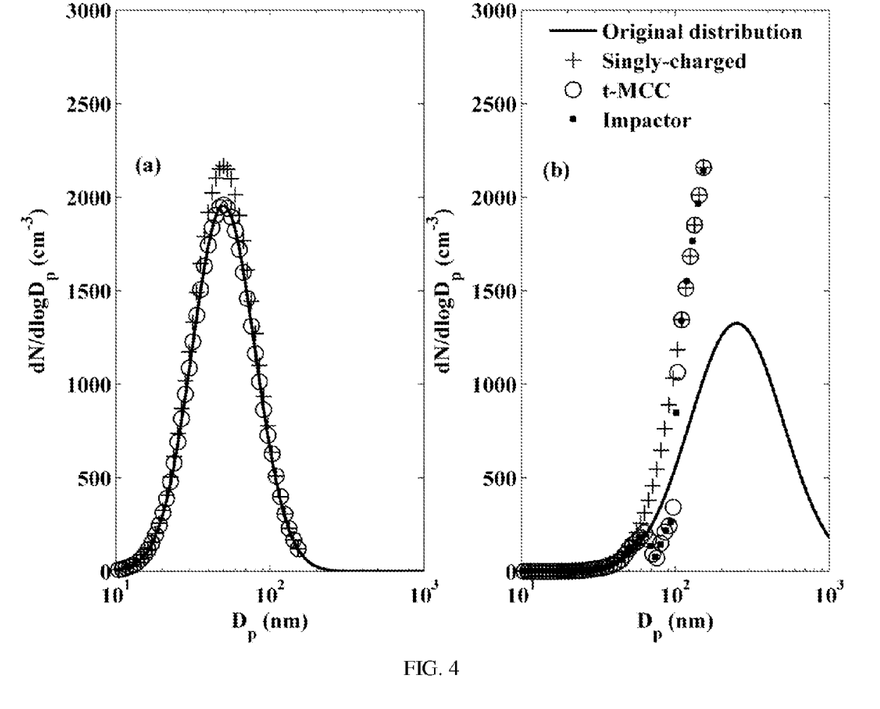
FIG. 4 is a graph representing the inversion of partial scan SEMS data using the traditional MCC method, where the SEMS operating conditions and the test particle size distributions are as listed in TABLE 1 below, where (a) is case C from TABLE 1 and; (b) is case D from TABLE 1.

Even if the particles are spherical and have unit density, if the DMA cannot be scanned to the highest voltage possible, then the impactor application is not ideal. A limited voltage scan range is especially applicable under conditions of high relative humidity or low pressure DMA operation. Under such conditions, the DMA voltages can only be partially scanned and thus, the impactor application will be non-ideal. For the scenario considered in cases C and D, the signals obtained with a partial voltage scan, with a maximum voltage of 2 kV, is inverted and the obtained particle size distribution is shown in FIG. 4. When the particles are largely in the ultrafine size range, the inverted particle size distribution is reasonably accurate (FIG. 4a), but when a significant fraction of particles are larger than 100 nm, then size distributions cannot be accurately calculated from partial voltage scan SEMS operation (FIG. 4b).

For SEMS data obtained under scenarios such as DMA operation without an impactor, mismatch between aerodynamic and electrical mobility sizes, and possible partial DMA voltage scan range, a robust approach to determine particle size distributions accounting for multiple charge correction is required.

A Fitted Multiple Charging Correction Method and Algorithm

Curve Fitting

Critical to accurate particle size distribution calculation from SEMS measurements is the accurate knowledge of the contribution of multiply-charged particles to the signal associated with singly-charged particle fraction. As the use of the impactor can complicate size distribution analysis, there is a continued need for an approach without an upstream impactor, in place. In described approach, the zeroth order, singly-charged distribution is fitted using an appropriate shape function such that the singly-charged distribution can be extended to sizes beyond the DMA scan range. The fitted distribution values beyond the scan range are then used to predict the multiple charge correction for the signals in the SEMS channel.

Figure 5:
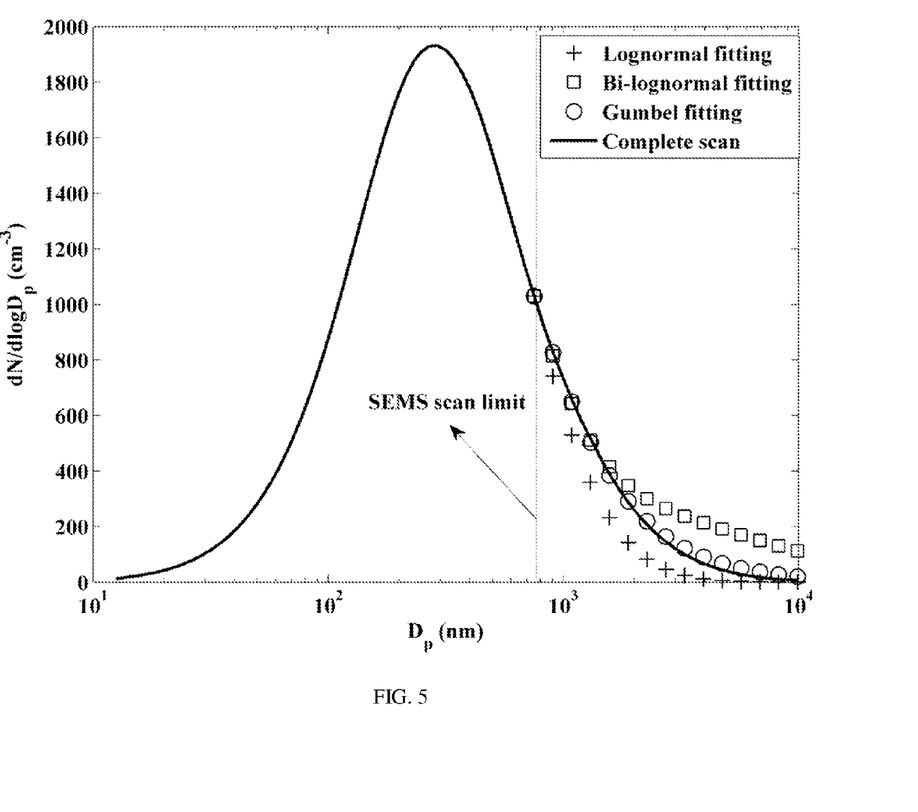
FIG. 5 is a graph representing the comparison of the quality of different functions used to extend the singly-charged size distribution obtained from a SEMS scan of a log-normal distribution of particles with median size of 250 nm and geometric standard deviation of 2.3, where the SEMS scan data are obtained using the case E conditions listed in TABLE 1, below.

For a wide range of possible size distributions, the zeroth order singly charged distributions will also have a wide range of possible shape functions. Herein is considered log-normal particle size distributions, but the approach is valid for broad range of size distribution shapes. To establish the shape of the zeroth order singly-charged size distribution, dN/d log $D_{p,i}$, corresponding to different initial log-normal shaped size distributions, SEMS operation without the constraint of an upper limit of DMA scan voltage, i.e. full scan, is considered. The partial zeroth order singly charged size distribution is then obtained considering a typical upper scan voltage limit of 10 kV and the partial scan data is fitted with different distribution functions, including, lognormal, bi-lognormal, and Gumbel, and the fitted distribution is compared against the expected distribution obtained from the full scan. Of the different fits, the Gumbel distribution is seen to result in the best fit, as shown in FIG. 5, although the other fits are possible as well, as are combinations.

The Gumbel distribution is a type of generalized extreme value distribution, and the particle size distribution represented by this function can be expressed as:

$$\frac{dN}{d\log D_p} = \frac{N_t}{\ln(\sigma_g)} e^{-\frac{\ln(D_p)-\ln(D_{pg})}{\ln(\sigma_g)} - e^{-\frac{\ln(D_p)-\ln(D_{pg})}{\ln(\sigma_g)}}} \quad \text{(Equation 18)}$$

where $N_t$ is particle total number concentration, $D_{pg}$ is the mode size, $\sigma_g$ is a scale parameter. When the lognormal and Gumbel distributions are applied to fit the same dataset, the parameters of the two distributions can be related as:

$$D_{pg} = \overline{D_{pl}} e^{\ln^2(\sigma_l)} \quad \text{(Equation 19)}$$

$$\ln(\sigma_g) = 0.72(\ln(D_{p84\%}) - \ln(D_{p50\%})) = 0.72 \ln(\sigma_l) \quad \text{(Equation 20)}$$

where $\overline{D_{pl}}$ and $\sigma_l$ are the geometric mean size and geometric standard deviation of the log-normal distribution, $D_{p50\%}$ and $p_{p84\%}$ are the particle sizes corresponding to 50% and 84% in the log-normal cumulative distribution function.

Fitted MCC Approach

A fitted multiple-charge correction (f-MCC) approach based on the Gumbel fit to the singly-charged size distribution is introduced. The different steps of the proposed f-MCC algorithm are:

1) Determine the zeroth order singly-charged distribution using Eq. 8 for the available SEMS channels.

Figure 6:
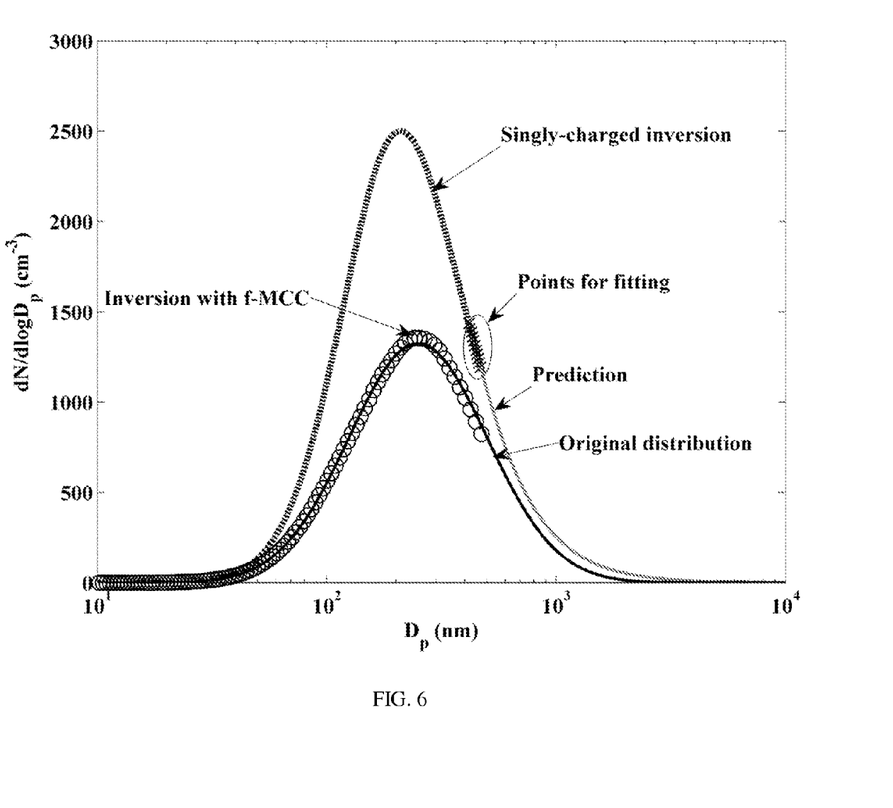
FIG. 6 is a graph representing the data points at the end of the scan range selected for fitting the singly-charged distribution are indicted and extended singly-charged size distribution obtained from Gumbel distribution is shown.

2) Use the Gumbel fit function to fit the zeroth order singly-charged size distribution to sizes beyond the DMA scan range. A particular challenge in fitting the distribution is to determine the extent of the data to be fit. As the fit function values are used only to estimate the singly-charged fraction beyond the DMA scan range, just a limited data set from the singly-charged distribution obtained in step 1 is required to determine the fit function. Using only a limited number of data points to determine the fit function parameters helps ensure that the choice of the Gumbel fit curve is applicable for a broad range of starting size distributions. To determine the appropriate number of fit points, the zeroth order singly charged size distribution is first interpolated into finer channels (~100 channels per decade) to obtain the distribution, $$\left.\frac{dN}{d\log D_{p,1}}\right|_{fine}$$

and this distribution fit within the following rules:
  a) If there is no mode size detected in this distribution or if the distribution values near the end of the scan range indicate the start of a separate mode, then the last channel will have the largest concentration value of the measured mode. Under such conditions, a minimal number of $$\left.\frac{dN}{d\log D_{p,1}}\right|_{fine}$$

distribution values are used to fit the curve (typically the last 5 points).
  b) If a mode is detected, but there are only a limited number of channels in the dN/d log $D_{p,1}$ distribution between the mode size and the last scan channel (less than 5 data points), then the fine distribution, $$\left.\frac{dN}{d\log D_{p,1}}\right|_{fine}$$

is fit considering data from just prior to the mode location with 4 points to the last channel.
  c) For all other cases, the last 11 data points of $$\left.\frac{dN}{d\log D_{p,1}}\right|_{fine}$$

are selected for the fit function.
To illustrate the above selection procedure, the scenario of case B is again considered. For this case, the data points selected for fitting are shown in FIG. 6. As the zeroth order singly charged distribution has only one mode and the last scan channel is significantly away from the mode size, the last 11 data points are selected for the fit, as dictated by condition (c) above.

3) After the selection of the number of fit data points, the starting guess values of $D_{pg}$, $\sigma_g$, and $N_t$ for the Gumbel distribution fit must be appropriately chosen. The particle size corresponding to the maximum concentration value is assigned as the starting guess value of $D_{pg}$, and the number concentration obtained from the integral of the singly charged size distribution dN/d log $D_{p,1}$ is chosen as the starting guest value of $N_t$. From our analysis, it was determined that the obtained curve fit distribution is not sensitive to the starting guess value of $\sigma_g$. The fit distribution parameters are then determined and the zeroth order, singly charged distribution function is extended from the last SEMS channel size to 10 μm. With the extended distribution, the concentration in the last size channel can be assumed to be zero. Using the procedure described in this step for case B scenario, the extension of the singly-charged size distribution to sizes larger than the scanned size range is shown in FIG. 6.

4) By combining the singly-charged distribution, dN/d log $D_{p,1}$ and the fit distribution beyond the scan range, an extended singly-charged size distribution $$\left.\frac{dN}{d\log D_{p,1}}\right|_{fine},$$

is obtained, with L (>M) number of total size channels. The traditional multiple-charge correction approach must then be applied to this extended singly-charged size distribution starting from the penultimate channel (L−1) and stepping backwards to the first channel, using Eqs. 13 and 14.

The use of the above approach for the inversion of the signals obtained for case B is shown in FIG. 6. The fitted MCC correction approach is seen to accurately account for the multiple charge contribution and retrieve an accurate size distribution from the SEMS signal. It must be noted here, that the proposed fit function approach can only be used to predict the likely contribution of the multiply-charged particles to the singly-charged distribution, but not to extend the size distribution calculation of particles beyond the singly-charged diameter range of the DMA. This is because, while the fit function is reasonably accurate for particle diameters close to the DMA scan range, its accuracy at larger sizes is not guaranteed.

Testing the Fitted MCC Approach

The applicability of the fitted MCC algorithm for SEMS data analysis must be established by testing its performance against a range of particle size distributions and DMA operating conditions. For these tests, the SEMS data are simulated by considering ideal DMA operation and the SEMS equation (Equation 3). The accuracy of the predictions from the algorithm will be established by calculating the error in the inverted size distribution, relative to the input size distribution. In addition to the simulation-based testing, the performance of the fitted MCC algorithm is also tested using experiment data.

Error Analysis

For all the simulation-based tests, the quality of the size distribution retrieved using the fitted MCC algorithm is compared against the original size distribution using the error definition:

$$\text{Error} = \frac{\sqrt{\sum\left(\left.\frac{dN}{d\log D_p}\right|_{MCC} - \left.\frac{dN}{d\log D_p}\right|_{original}\right)^2}}{\sqrt{\sum\left(\left.\frac{dN}{d\log D_p}\right|_{original}\right)^2}} \quad \text{(Equation 20)}$$

Figure 7:
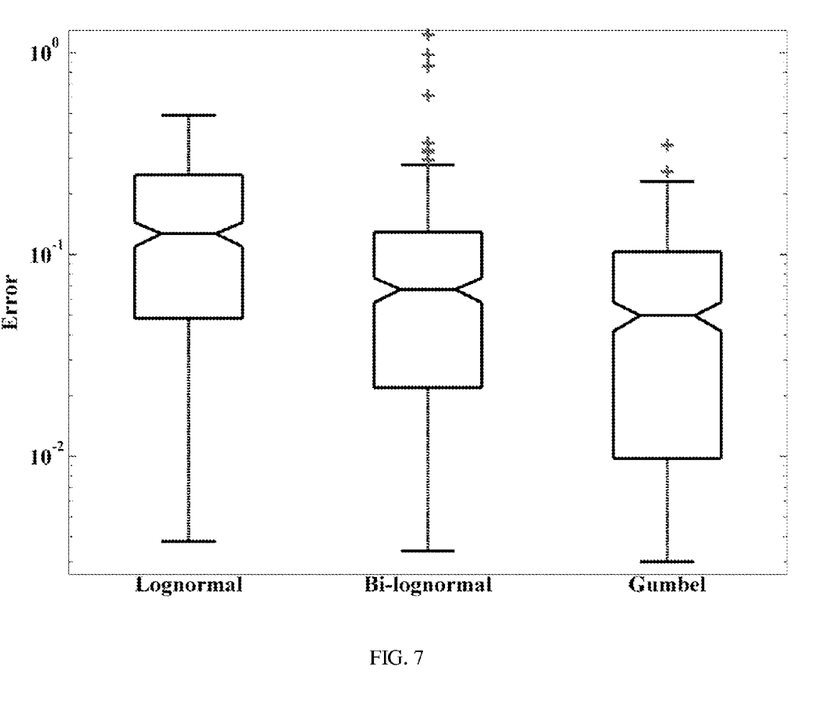
FIG. 7 is a graph representing the comparison of net error in the retrieved size distribution (calculated using Equation 21, below) for lognormal, bi-lognormal, and Gumbel functions used to fit the singly-charged distribution, where the conditions used for the test are listed as case E in TABLE 1, below.

In the first set of tests, a parametric study is conducted by varying the log-normal parameters of the input particle size distribution—geometric mean size from 40 to 800 nm and geometric standard deviation from 1.1 to 3.1, and the SEMS is operated with the conditions listed as case E in TABLE 1. First the singly charged size distributions, dN/d log $D_{p,1}$, are obtained from Eq. 8. Then, using the fitting rules described in the second step above, the singly charged distribution, dN/d log $D_{p,1}$, is fit using three distributions—log-normal, bi-lognormal, and Gumbel functions. Size distributions are then calculated following the steps 3 and 4 of section 3.2. The errors in the calculated size distributions relative to the original size distributions are established using Eq. 21 for all the test cases, and the results are shown in FIG. 7. For the entire range of input size distributions studied, the Gumbel fit distribution is seen to result in the least error and the lognormal fitting results in the largest error. This is because, the net contribution of singly and multiply charged particles increases with particle size, resulting in skewing the singly charged size distribution to the larger diameters. This skewed distribution is better represented by the Gumbel distribution than the other two distributions studied.

Figure 8:
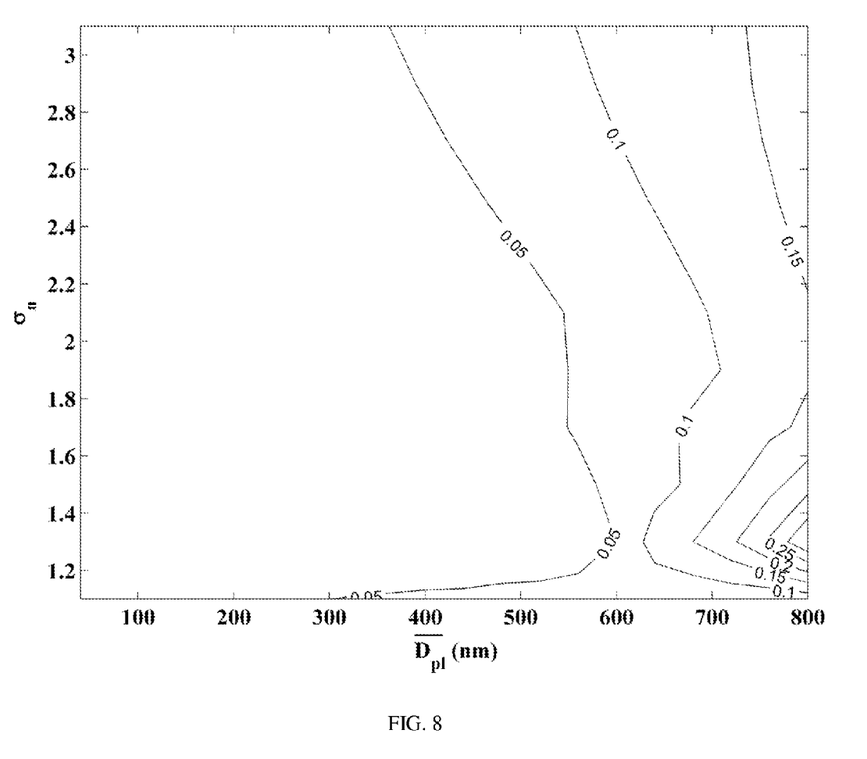
FIG. 8 is a graph representing error contours for varying log-normal parameters of the original distribution and Gumbel fitting of the singly-charged distribution, where the conditions used for the test are listed as case E in TABLE 1, below.

The accuracy of the fitted MCC approach with the Gumbel distribution for varying log-normal parameters of the input size distribution is shown in FIG. 8. The errors in the calculated size distributions are maximal at the highest geometric mean sizes and when the sampled size distribution is very narrow. When the geometric mean diameters are smaller than 300 nm, the errors are negligible, independent of the $\sigma_n$ value. In general, the proposed fitted MCC approach results in an error of less than 10% for almost the entire range of size distributions studied.

Experiment Validation

Figure 9:
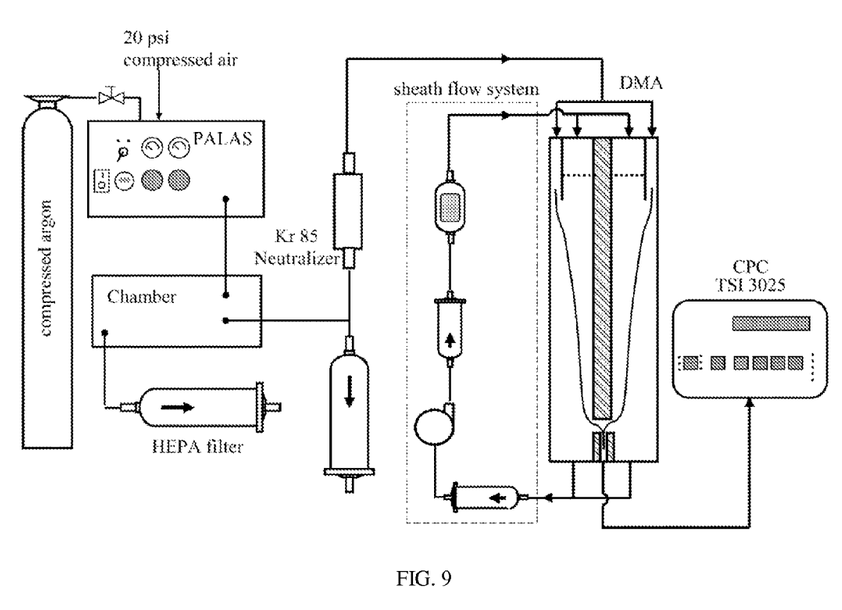
FIG. 9 is a schematic diagram of an experimental test setup used to obtain data to validate the performance of the f-MCC approach according to an embodiment.

In addition to testing the fitted MCC approach with simulated SEMS data, the validity of the method is also tested with experimental data. Experiment data for testing the inversion algorithm was obtained using the setup shown in FIG. 9. A polydisperse distribution of particles was produced using a spark generator (GFG-1000, Palas Gmbh). The spark generator is operated at high frequency (~950 Hz) to ensure that the particles produced have a mode size >100 nm, and thus, when passed through a diffusion charger, a significant fraction of these particles will be multiply-charged. The total particle number concentrations were nearly constant during the entire measurement period, suggesting stable aerosol generation. The particles were sampled into a TSI long-DMA (TSI 3071), and the size distribution of these particles was first obtained by a slow scan SEMS operation (scan time of 240 s) over a voltage range of 10 to 9,600 V. The choice of slow-scanning ensured that the SEMS data were not affected by smearing effects associated with scanning DMA operation. The DMA is operated under balanced flow conditions, with sheath and aerosol flows of 6.17 and 1.0 lpm, respectively, and without an impactor in the sample flow. The classified particles sampled out of the DMA are detected by a TSI 3025 CPC. The data from this experiment, with the voltage scanned from 10 to 9,600 V, will be referred to as full-scan data. The experiment is then repeated under identical conditions, with one primary difference: the voltage scan range is reduced to 10 to 2000 V. The data obtained from this scan is referred to as partial scan. The SEMS channel data obtained from the two cases are inverted to obtain size distributions of the sampled particles using three approaches: zeroth order inversion assuming singly charging (singly-charged), traditional MCC approach (t-MCC) and the new fitted MCC approach (f-MCC).

For the full-scan case, the concentration of classified particles in the last channel is low, suggesting a near full-voltage-scan operation of the SEMS. As almost the entire particle size distribution is covered by the DMA scan during this test, an accurate size distribution considering the multiple-charging contribution should be possible with the t-MCC method. A comparison of the distributions obtained using the three inversion approaches (singly-charged, t-MCC, and f-MCC) is shown in FIG. 10.

As expected, the size distributions obtained using the t-MCC and f-MCC approaches are almost identical, while the presence of a significant fraction of multiply-charged particles makes the singly-charged distribution highly inaccurate.

Figure 10:
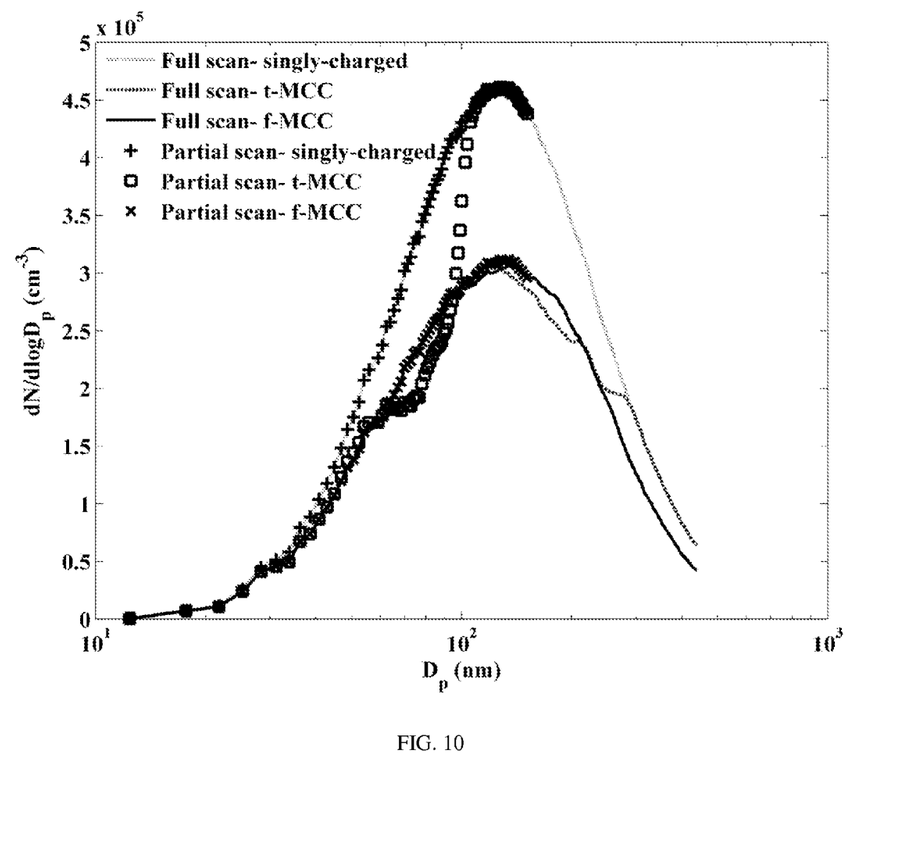
FIG. 10 is a graph representing the comparison of the inverted size distributions obtained from full and partial voltage scan SEMS data considering the different inversion approaches of: singly-charged, t-MCC, and f-MCC.

The size distributions calculated from the partial scan SEMS data using the three approaches are also shown in FIG. 10. As the experiments were conducted with stable particle generation, the size distributions from the partial-scan case must match those obtained from the full-scan experiments. As expected, the singly-charged size distributions are completely inaccurate. The size distribution calculated using the t-MCC method is also very inaccurate. The inability to account for the contribution of multiply-charged particles to the last few SEMS channel results in erroneous correction to the singly charged size distribution for almost all size channels and results in an inaccurate multi-modal distribution. The new f-MCC is seen to correctly account for the multiple charge contribution to all the channels and result in an accurately calculated size distribution.

Application of the f-MCC Method

The use of the f-MCC approach is, thus, shown to result in reasonably accurate size distribution retrieval for a range of test distribution shapes (FIG. 6) and voltage scan ranges (FIG. 10). There may be, however, some extreme cases where the application of the new f-MCC algorithm results in erroneous results. For example, if two distinct particle modes exist, with one mode almost completely beyond the scan range, the f-MCC approach cannot provide accurate size distributions. If the second mode is only very minimally captured in the DMA scan, again very erroneous results are possible. Except for these very extreme test conditions, the f-MCC inversion approach has seen to be quite robust for size distribution retrieval from SEMS measurements. Using the f-MCC inversion algorithm for analysis of data from a SEMS systems operated with an impactor might provide additional information about the density or shape factor of the sampled particles.

Although the present invention has been described in connection with a preferred embodiment, it should be understood that modifications, alterations, and additions can be made to the invention without departing from the scope of the invention as defined by the claims.

What is claimed is:

1. A method for determining particle size distribution from electrical mobility spectrometry (EMS) measurements in the presence of multiply charged particles, the method comprising the steps of:
   obtaining, via an electrical mobility spectrometer, EMS data, wherein the received EMS data comprises a particle signal for one or more EMS channels;
   calculating, using a processor, a zeroth order singly-charged particle size distribution from the particle signals in the one or more EMS channels;
   fitting, by the processor using a distribution function, the calculated zeroth order singly-charged particle size distribution to obtain a fit function value;
   correcting, by the processor using the obtained fit function value, for multiply-charged particle contribution to the received EMS data; and
   providing an output to a user comprising the fit and corrected particle size distribution.

2. The method of claim 1, wherein said EMS data is obtained using a scanning electrical mobility spectrometer.

3. The method of claim 1, wherein said EMS data is obtained without the use of an inertial impactor.

4. The method of claim 1, wherein said distribution function is a Gumbel distribution function.

5. The method of claim 1, wherein said distribution function is a lognormal or a bi-lognormal distribution function.

6. The method of claim 1, further comprising the step of interpolating the obtained zeroth order singly-charged particle size distribution into one or more finer channels to determine an appropriate number of fit points for said fitting step.

7. The method of claim 6, wherein if said interpolation determines that there is no detected mode size, or if said interpolation determines that a separate mode is beginning near the end of the obtained SMS data, then approximately the last 5 data points are used for said fitting step.

8. The method of claim 7, wherein said distribution function is a Gumbel distribution function, and further comprising the step of determining an initial value for $D_{pg}$, $\sigma_g$, and $N_t$ for the Gumbel distribution function, where $N_t$ is particle total number concentration, $D_{pg}$ is the mode size, and $\sigma_g$ is a scale parameter.

9. The method of claim 8, wherein said initial value for $D_{pg}$ is equal to a particle size with the maximum concentration value.

10. The method of claim 8, wherein said initial value for $N_t$ is a number concentration obtained from an integral of the singly-charged distribution $dN/d \log D_{p,1}$.

11. The method of claim 1, wherein said correcting step is performed using multiple-charge correction.

12. The method of claim 1, further comprising the step of obtaining said EMS data using an EMS.

13. A non-transitory machine readable storage medium having stored thereon a computer program for determining particle size distribution from electrical mobility spectrometry (EMS) measurements in the presence of multiply charged particles, the computer program comprising instructions for causing the machine to perform the steps of:
obtaining, via an electrical mobility spectrometer, EMS data, wherein the received EMS data comprises a particle signal for one or more EMS channels;
calculating a zeroth order singly-charged particle size distribution from the particle signals in the one or more EMS channels;
fitting, using a distribution function, the calculated zeroth order singly-charged particle size distribution to obtain a fit function value;
correcting, using the obtained fit function value, for multiply-charged particle contribution to the received EMS data; and
providing an output to a user comprising the fit and corrected particle size distribution.

14. The non-transitory machine readable storage medium of claim 13, wherein said distribution function is a Gumbel distribution function.

15. The non-transitory machine readable storage medium of claim 13, wherein the computer program further comprises instructions for causing the machine to interpolate the obtained zeroth order singly-charged particle size distribution information into one or more finer channels to determine an appropriate number of fit points for said fitting step.

16. A system configured to determine particle size distribution from electrical mobility spectrometry (EMS) measurements in the presence of multiply charged particles, the system comprising:
an electrical mobility spectrometer configured to obtain EMS data, wherein the received EMS data comprises a particle signal for one or more EMS channels;
a processor configured to:
calculate a zeroth order singly-charged particle size distribution from the particle signals in the one or more EMS channels;
fit, using a distribution function, the calculated zeroth order singly-charged particle size distribution to obtain a fit function value; and
correct, using the obtained fit function value, for multiply-charged particle contribution to the received EMS data; and
provide an output to a user comprising the fit and corrected particle size distribution.

17. The system of claim 16, wherein said EMS data is obtained using a scanning electrical mobility spectrometer.

18. The system of claim 16, wherein said EMS data is obtained without the use of an inertial impactor.

19. The system of claim 16, wherein said distribution function is a Gumbel distribution function.

20. The system of claim 16, wherein said processor is further configured to interpolate the obtained zeroth order singly-charged particle size distribution information into one or more finer channels to determine an appropriate number of fit points for said fitting step.

* * * * *